United States Patent [19]

Anspach, Jr. et al.

[11] Patent Number: 5,326,205
[45] Date of Patent: Jul. 5, 1994

[54] EXPANDABLE RIVET ASSEMBLY

[76] Inventors: William E. Anspach, Jr., 1349 S. Killian Dr., Lake Park, Fla. 33403; William S. Reid, Ste. 550, Professional Office Bldg., 1932 Alcoa Hwy., Knoxville, Tenn. 37920; Eddy H. Del Rio, 11413 52nd Rd. N., Royal Palm Beach, Fla. 33411

[21] Appl. No.: 889,477

[22] Filed: May 27, 1992

[51] Int. Cl.[5] .................... F16B 13/04; F16B 13/06
[52] U.S. Cl. ............................ 411/43; 411/38; 411/59; 606/74
[58] Field of Search .................... 411/34, 36-38, 411/43, 59, 60, 61; 606/72, 74

[56]  References Cited

U.S. PATENT DOCUMENTS

| | | | |
|---|---|---|---|
| 3,143,916 | 8/1964 | Rice | 411/37 |
| 3,779,239 | 12/1973 | Fischer et al. | 411/38 X |
| 3,896,504 | 7/1975 | Fischer | 411/38 X |
| 4,355,934 | 10/1982 | Denham et al. | 411/43 X |
| 4,580,936 | 4/1986 | Francis et al. | 411/43 X |
| 4,696,610 | 9/1987 | Wright | 411/43 X |
| 4,752,168 | 6/1988 | Richter | 411/38 |
| 5,030,050 | 7/1991 | Auriol et al. | 411/43 X |

*Primary Examiner*—Neill R. Wilson
*Attorney, Agent, or Firm*—Jack N. McCarthy

[57]  ABSTRACT

An expandable rivet assembly for attaching objects, especially when using bone. The assembly includes a rivet and puller where the puller is pulled to expand the rivet. A stop is provided in the rivet to set an upper limit to the expansion of the rivet by the puller. This rivet is useful in material of varying density, and has slots on the side and a contoured surface to initiate bending at a desired location.

9 Claims, 10 Drawing Sheets

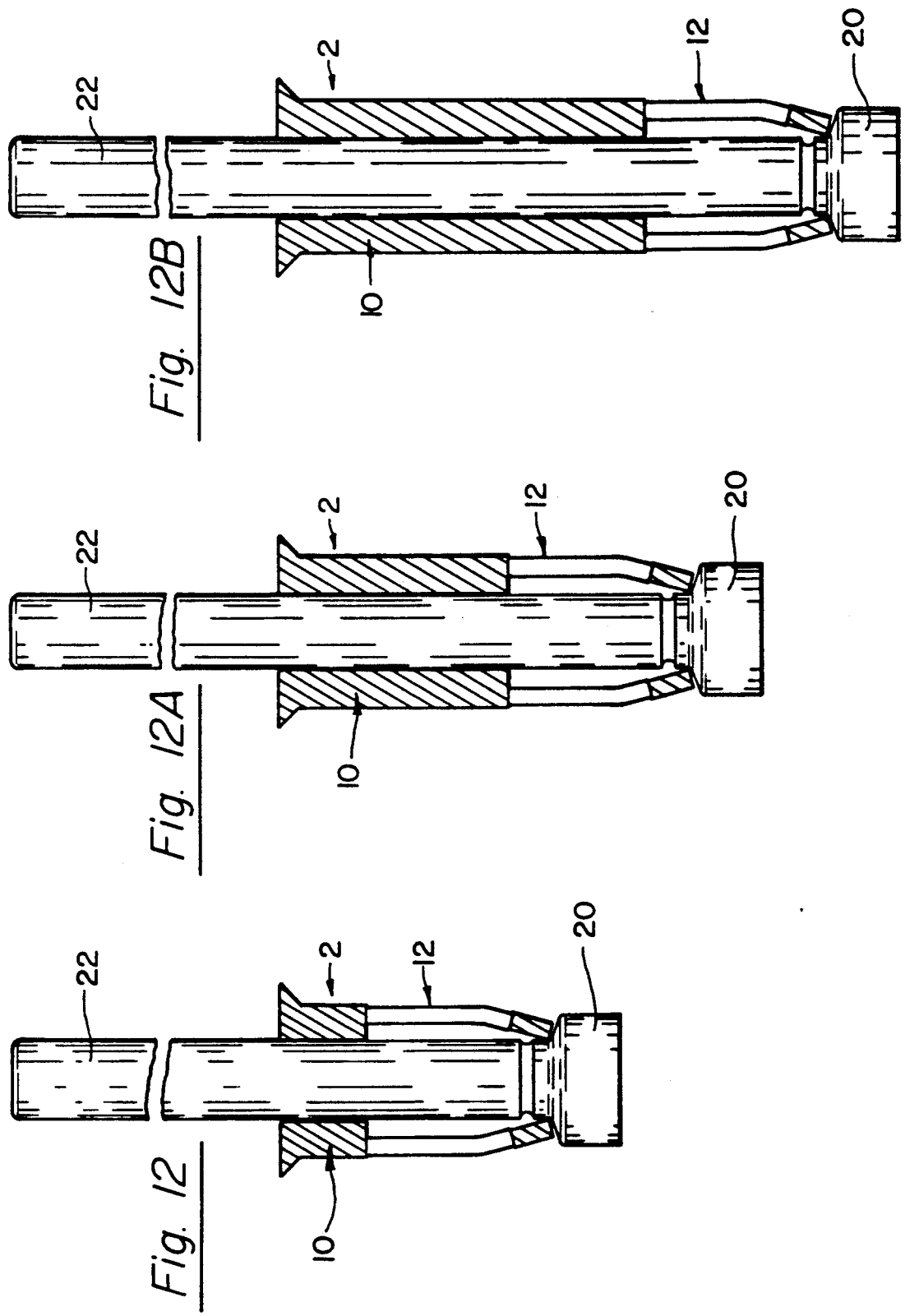

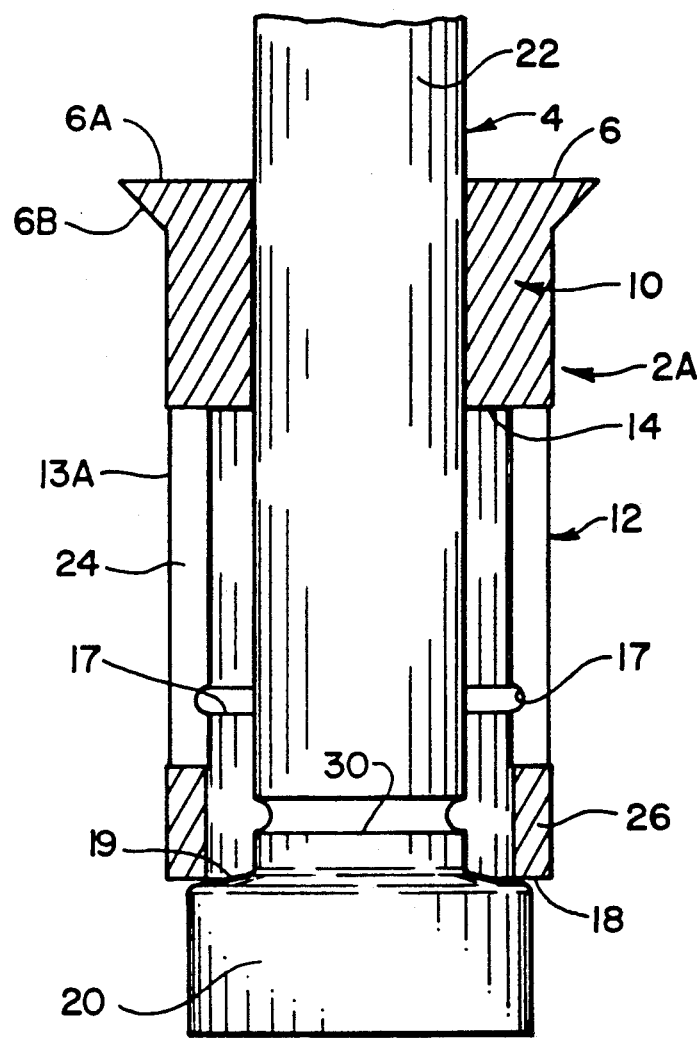

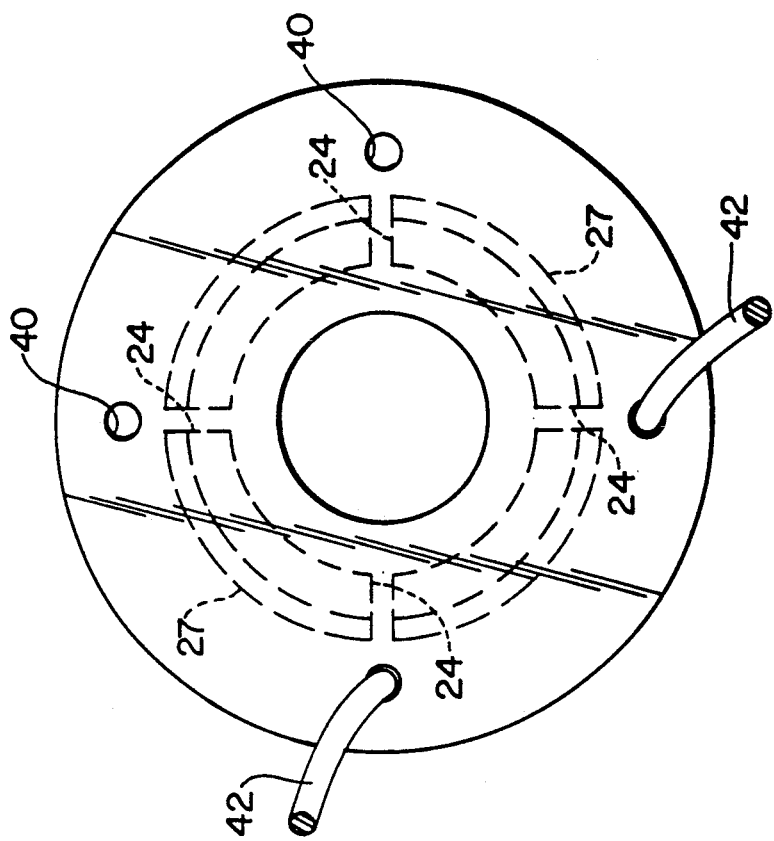
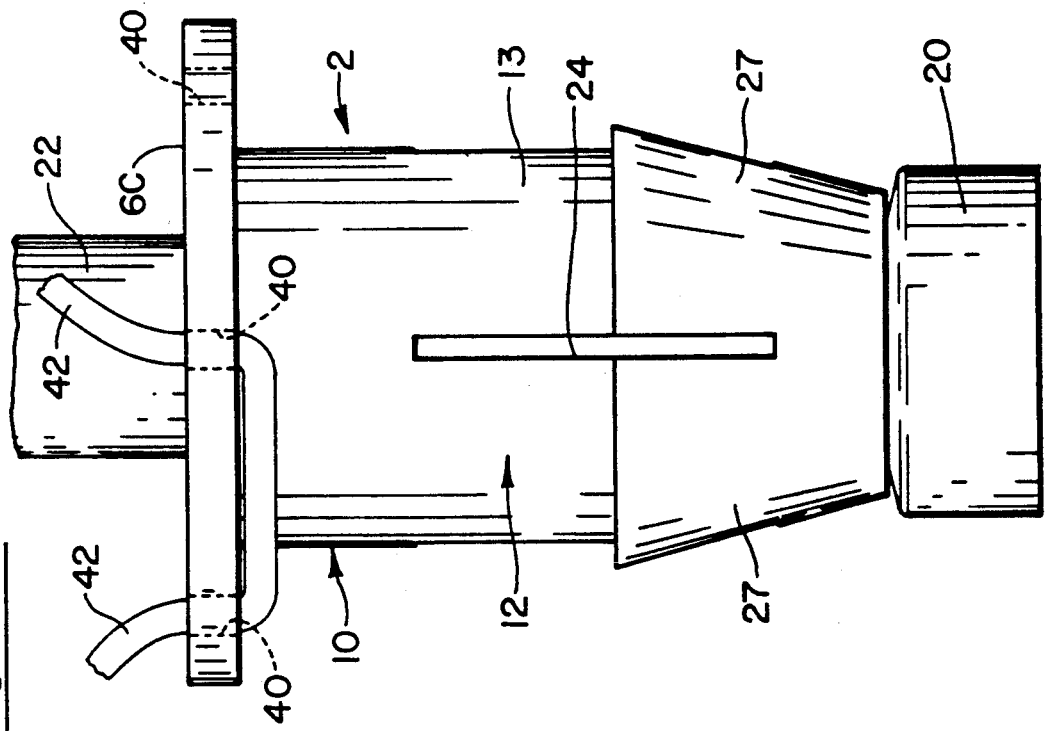

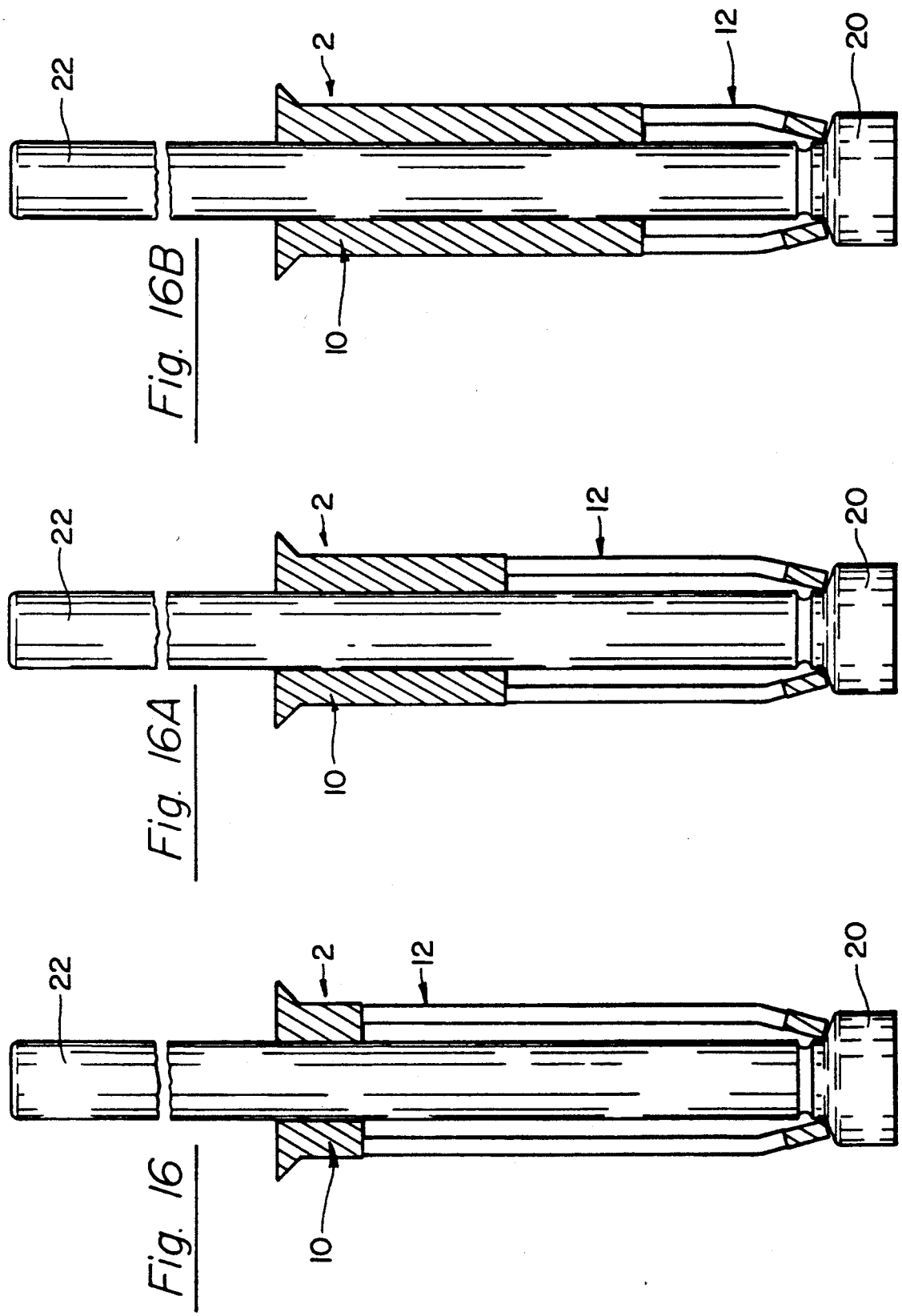

EXPANDABLE RIVET ASSEMBLY

TECHNICAL FIELD

The invention relates to a device for attaching metallic or synthetic plates and sutures to bone.

BACKGROUND OF THE INVENTION

The most common fastener used in the reconstruction of fracture fragments in the human body is a screw. Screws of various types are used to directly hold fragments together, hold plates onto bone, and to act as anchors for the attachment of tendons and grafts of various types. Screws have certain disadvantages. In soft bone, they gain little purchase; in extremely thin bone, such as about the face, few threads gain purchase for adequate fixation. With the advent of extremely small bone plates for fracture and reconstructive surgical procedures, the screws are so small that just handling them and keeping them on a screwdriver can be difficult. Screws also require a significant amount of time to insert, especially if the hole has to be threaded first.

Various types of "blind" rivets are commonly used in industry. Most of them consist of two parts: a puller and the rivet body. The puller causes a deformation of the rivet body as it is moved in a linear direction. The expansion deformity of the rivet body continues until the expanded area reaches either the rivet head or the material into which the rivet is placed. These types of fasteners work well in sheet metal as the material has sufficient strength to resist further deformation of the rivet body and tight fixation, as well as breakaway of the puller shaft is accomplished quite easily. Unfortunately, these designs do not work well in the human body, as bone is not strong enough to stop the progression of the widened rivet body before it contacts the rivet head.

Patents related to the subject matter are the following: U.S. Pat. Nos. 1,105,105; 2,494,229; and 4,590,928.

DISCLOSURE OF THE INVENTION

The object of the present invention is to create a rivet fastener which will be effective for attachment in all types of bone and which will contribute significantly to the ease and rapidity of the procedure. To gain maximum expansion of the rivet body, the body is slotted longitudinally with the bottom portion tapered inwardly so that when it is forced to expand by a puller head, it will form radial wings, or arms, which will extend into soft bone, but just expand radially without forming wings, or arms, in harder bone. The wings, or arms, are forced to be created at a distance below the surface of the bone as determined by a tapered-in portion in the rivet body. Local thinning out or notching the rivet wall results in a similar rivet deformation. Complete deformation of the rivet body to the rivet head is prevented by a puller head stop. The design creates a "blind" rivet which is extremely effective for attaching objects to bone.

Another object of the invention is to provide a suture attachment to bone. This can be used for transplantation of tendons, re-attachment of muscles, and basically any needed fixation to bone.

Besides the intended application in the medical field, which requires the use of bio-compatible metals to be used exclusively, there is also a potential application in industry, where a variety of metals can be used to optimize specific requirements for fastening metals, plastics and wood. A combination of different metals and rivet geometry variations (i.e. steel puller and aluminum rivet) can be used to obtain modified rivet behavior to satisfy industrial applications.

BRIEF DESCRIPTION OF DRAWINGS

FIGS. 12, 12A and 12B show bone rivets of different lengths with equal lengths of the lower annular portions;

FIG. 13 is a cross-sectional view of a modified bone rivet;

FIG. 14 is a view similar to FIG. 9 showing a modified bone rivet with holding barbs, and showing a suture threaded through the top flange;

FIG. 15 is a top view of FIG. 14; and

FIGS. 16, 16A and 16B show rivets of the same length with different lengths of the lower annular portions and upper annular portions.

BEST MODE FOR CARRYING OUT THE INVENTION

Figure 2:
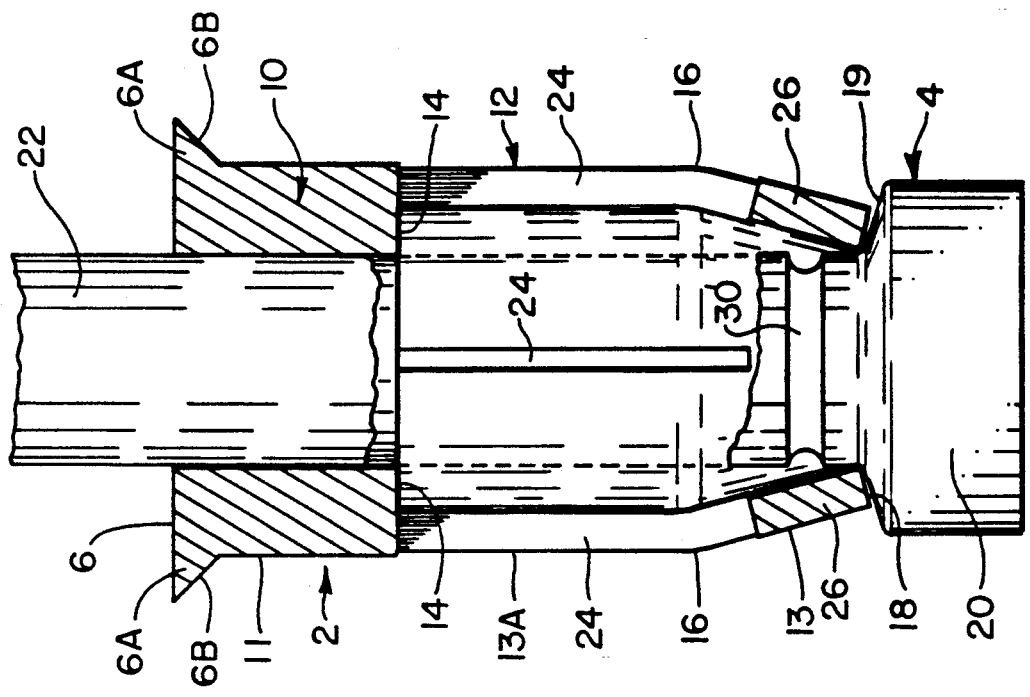
FIG. 2 is a cross-sectional view of the rivet taken along the line 2—2 of FIG. 1.
Figure 1:
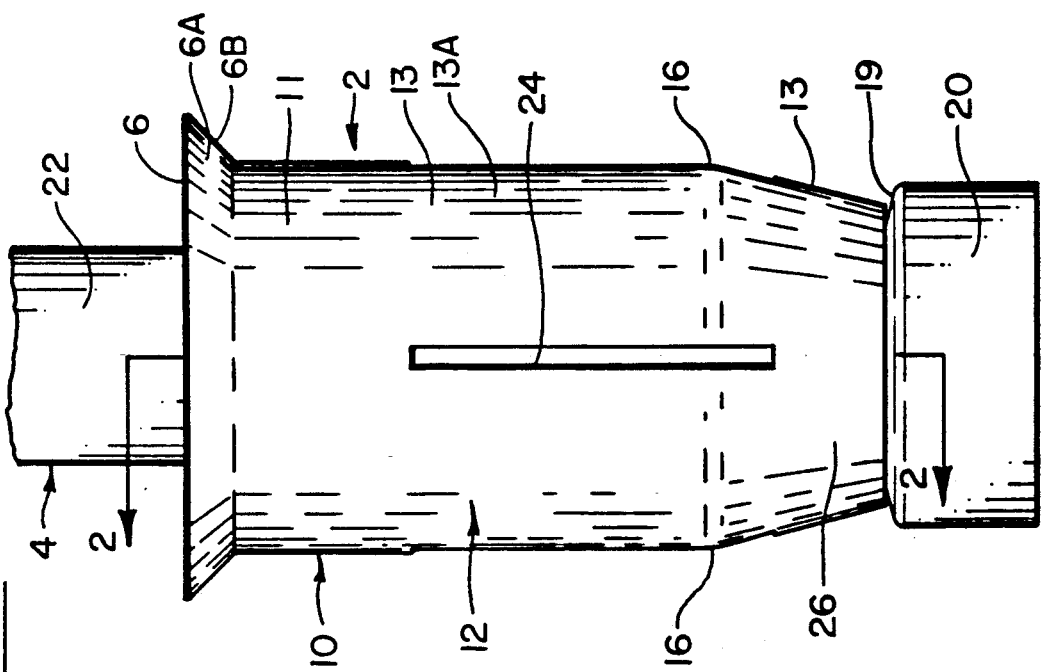
FIG. 1 is a side view of the bone rivet with the puller in place.
Figure 4:
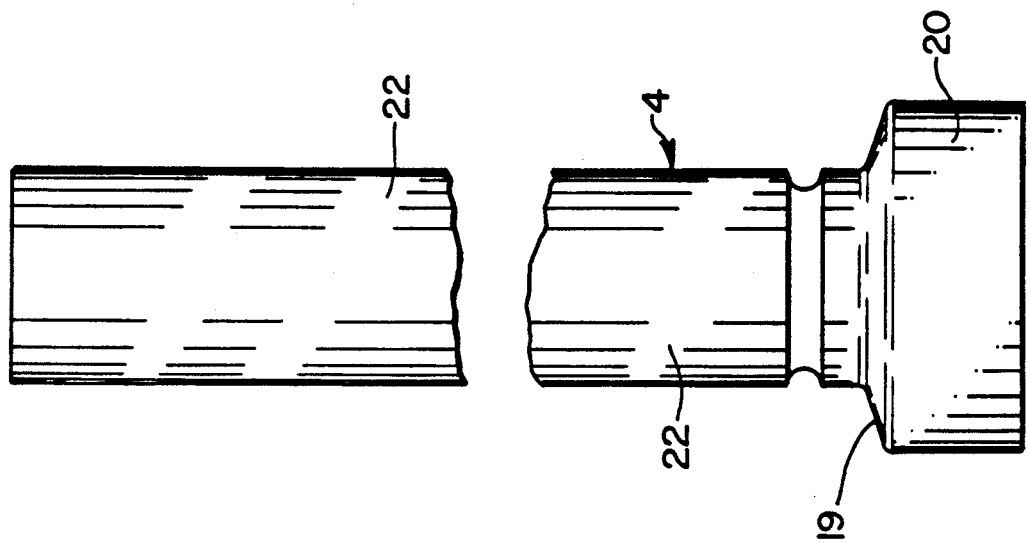
FIG. 4 is a side view of the puller.
Figure 3:
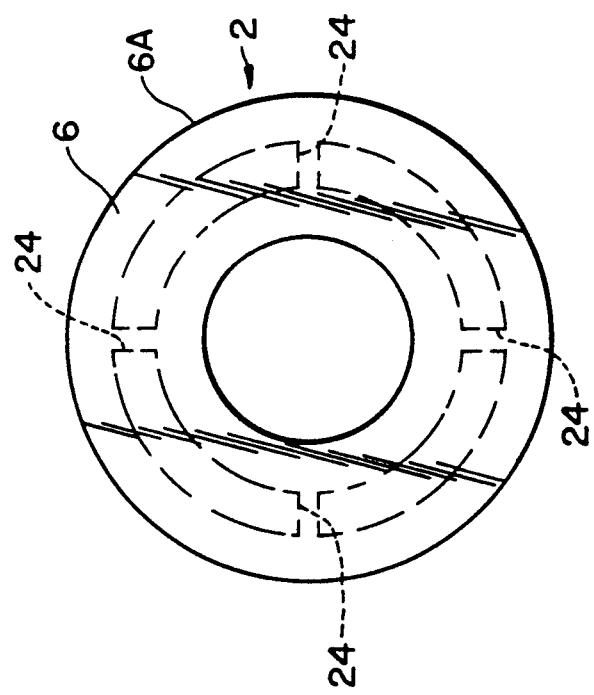
FIG. 3 is a top view of FIG. 2.
Figure 6:
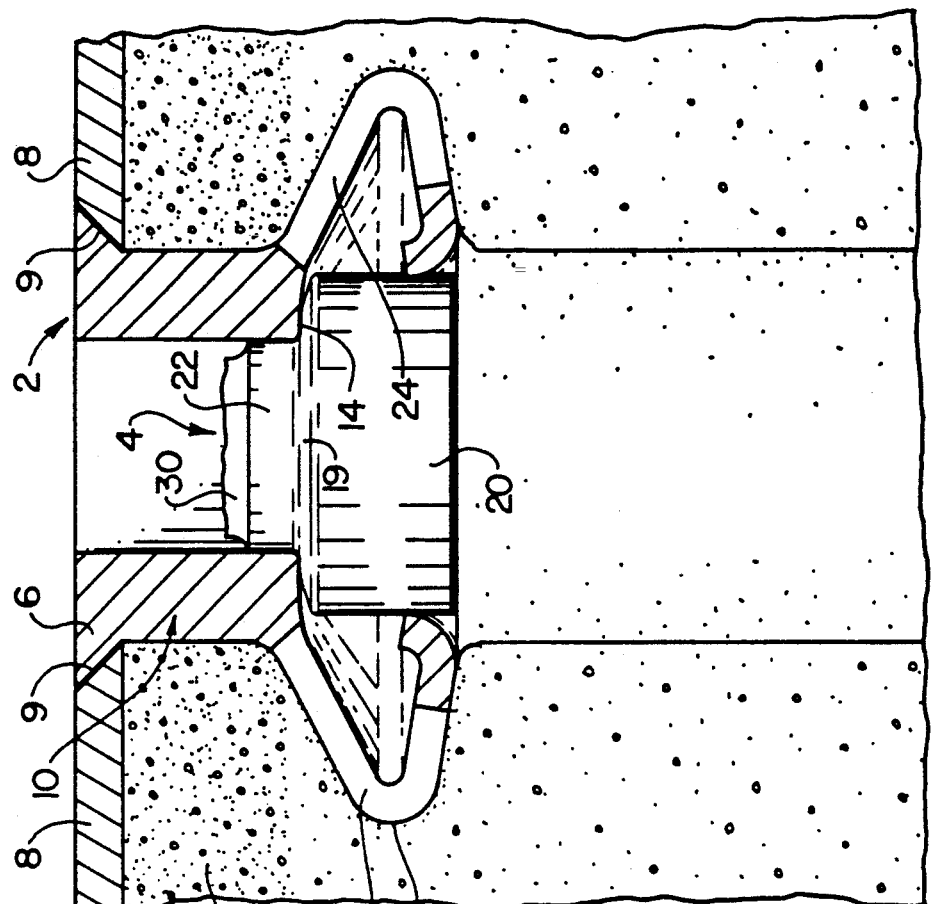
FIG. 6 is a sectional view of a bone rivet in place through a hole in an attaching plate, in a hole in "soft" bone with the broken-off head of the puller.
Figure 5:
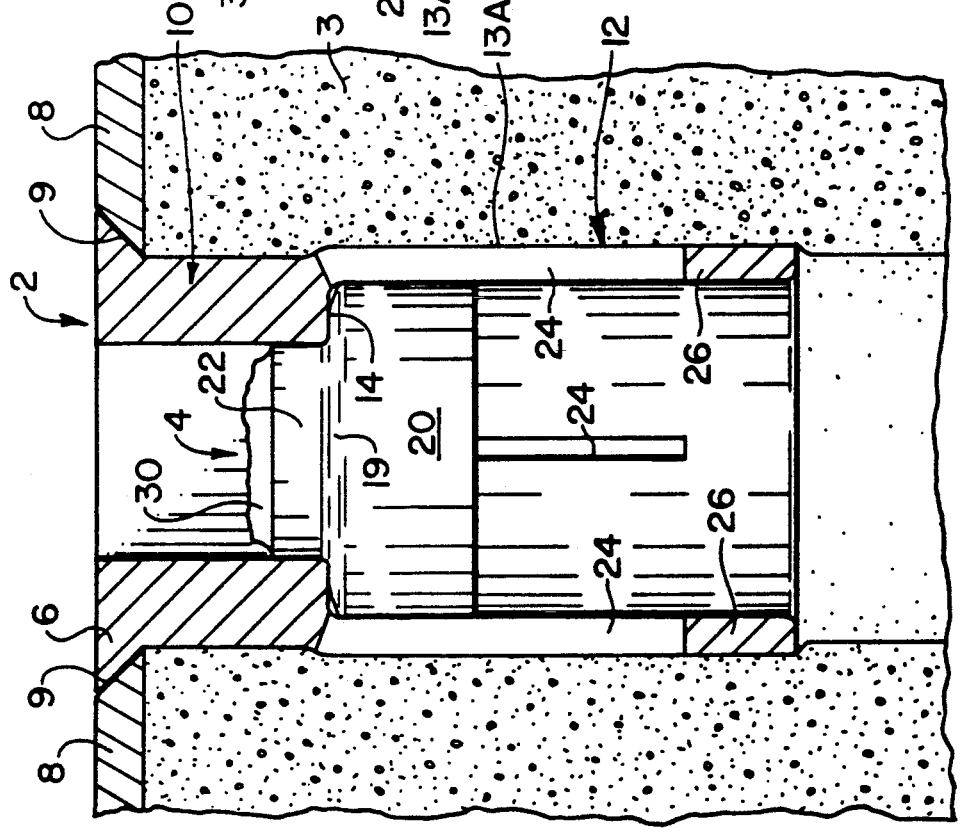
FIG. 5 is a sectional view of a bone rivet place, through a hole in an attaching plate, in a hole in "hard" bone with the broken-off head of the puller.

Referring to FIG. 1, a bone rivet 2 is shown having a puller member 4 located therewith. Puller member 4 comprises a puller head 20 and a puller rod 22. FIG. 2 is a section taken lengthwise through the center of the bone rivet 2 showing details of the bone rivet 2 and puller member 4. Examples of the bone rivet 2 positioned in place in bones 3 of different hardness are shown in FIGS. 5 and 6.

The bone rivet 2 has an upper annular portion 20 with a head 6 formed at the top thereof. Said head 6 has an annular flange 6A extending radially outwardly from around the top of the upper annular portion 10. A tapered surface 6B extends from the outer edge of the annular flange 6A downwardly and inwardly to the outer surface 11 of the upper annular portion 10 for a purpose to be hereinafter described.

The bone rivet 2 has a lower annular portion 12 extending downwardly from the bottom of the upper annular portion 10. Lower annular portion 12 has its outer surface 13 formed as an extension of outer surface 11 of upper annular portion 10. The thickness of the lower annular portion 12 is smaller than the thickness of the upper annular portion 10 forming an annular step, or stop, 14, for a purpose to be hereinafter described.

The lower part of the lower annular portion 12 is bent inwardly at a circumferential bend line 16 and extends to the end forming an opening at the bottom of the lower annular portion 12 having an inner diameter which is approximately equal to that of the inner diameter of the upper annular portion 10. The puller rod 22 extends upwardly through the inner diameter of the lower part of the annular portion 12 and the inner diameter of the upper annular portion 10.

It is noted that the lower end surface 18 of the lower annular portion 12 is shown angled downwardly and outwardly from its inner edge. It is this surface which faces the slightly angled top surface 19 of the puller head 20. A plurality of slots 24 is formed in the lower annular portion 12 forming lengthwise ribs 13A from the bottom of the upper annular portion 10, in line with the annular step, or stop, 14, to below the circumferential line 16 at which the lower annular portion 12 tapers inwardly leaving a solid tapered portion 26 at the lower end of the lower annular portion 12. It is this solid tapered portion 26 which ends in lower end surface 18. The top surface 19 of the puller head 20 is formed, slightly angled downwardly from the puller rod 22, to aid in guiding the lower end surface 18 of the lower annular portion 12 outwardly if the bone 3 does not permit the top surface 19 of the puller head 20 to force the ribs 13A of the lower annular portion 12, between the slots 24, outwardly so as to project into the bone 3 as arms (see FIG. 6). If bone resistance prevents the lower annular portion 12 from bending so that the ribs 13A enter the bone as radially extending arms, the bottom of the solid tapered portion 26 is expanded radially by the action of the top surface 19 of the puller head 20 against the bottom surface 18 to accept the puller head 20 within the lower annular portion 12 for movement upwardly to expand all of the lower annular portion 12 until it contacts the annular step, or stop, 14 (see FIG. 5).

The puller rod 22 is undercut at 30 to provide a weakened point along the puller rod 22 at which point the puller rod 22 will break when the top surface 19 of the puller head engages the step, or stop, 14, and the bone rivet 2 has been fixed in place in the bone 3. The two-part bone rivet assembly, the rivet 2 and puller member 4, is formed of a bio-compatible material. In a bone rivet assembly made, the rivet 2 was machined from a cylinder of titanium, and the puller member 4 was formed of cold forged titanium. The outer diameter of the puller rod 22 and the inner diameter of the end of the rivet 2 are sized for an interference fit so that the rivet 2 and puller member 4 remain as one unit, or assembly, before use. Other means can be used to maintain a rivet 2 and puller member 4 together, if desired, such as between the upper annular portion 10 of the rivet 2 and the puller rod 22.

In use, a surgical instrument is placed over the free end of the puller rod 22 and placed against the head 6 of the bone rivet 2. The instrument then grasps the puller rod 22 and pulls it upwardly to react with the lower portion 12 of the bone rivet 2. The reaction of the top surface 19 of the puller head 20 against the lower end surface 18 of the lower annular portion 12 deforms the lengthwise ribs 13A of the lower annular portion 12 differently, depending on the structure of the bone 3 being operated on.

This is shown in FIGS. 5 and 6, where in FIG. 5, the bone rivet 2 is in place in a hole in "hard" bone where the lengthwise ribs 13A of the lower annular portion 12 are merely radially cylindrically expanded without having a radial deformation form at a circumferential line 16 and enter the bone 3. The top surface 19 of the puller head 20 forces the solid tapered portion 26 outwardly and compresses it in the bone 3 and moves upwardly to compress all of the lengthwise ribs 13A of the lower annular portion 12 in the bone 3.

In FIG. 6, the bone rivet 2 is in place in a hole in "soft" bone, where the lengthwise ribs 13A of the lower annular portion 12 have been forced radially outward by the top surface 19 at the circumferential line 16 to enter the bone 3. Other means can be used to start bending at a desired location such as by an undercut section or locally thinned section (see FIG. 13). It can be seen that the plurality of slots 24 will permit a plurality of ribs 13A to extend as arms outwardly.

While "hard" and "soft" bones 3 have been discussed as examples, it is to be understood that the hardness of a bone can lie anywhere in the range between a "hard" bone which permits only a radial expansion of the lower annular portion 12 of the bone rivet into the bone 3, and a "soft" bone which permits the lower annular portion 12 to be bent and extend into the bone 3; all expansions providing the necessary holding strength.

The location of the expanded portion of the rivet 2 below the surface of the bone is determined by the length of the upper annular portion 10. Bone rivet assemblies of bone rivet 2 and puller member 4 having different lengths are shown in FIGS. 12A, 12B and 12C, and shown in use in a bone graft in FIG. 11.

Figure 7:
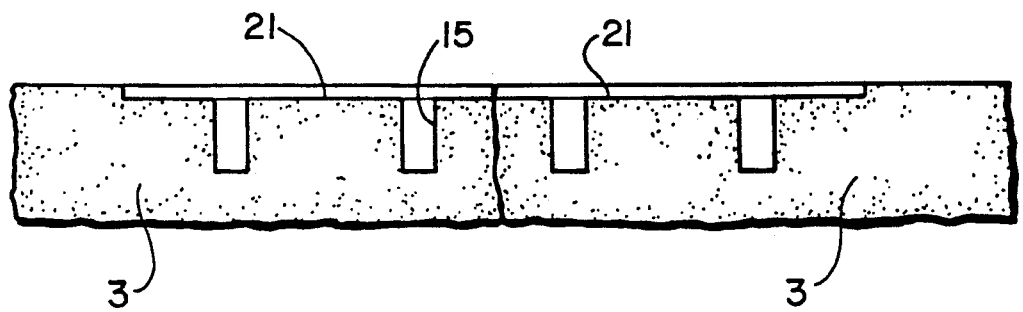
FIG. 7 is a cross-sectional view through two sections of bone which have been broken, prepared with a recess for receiving an attaching plate, and prepared with holes to receive bone rivets.
Figure 8:
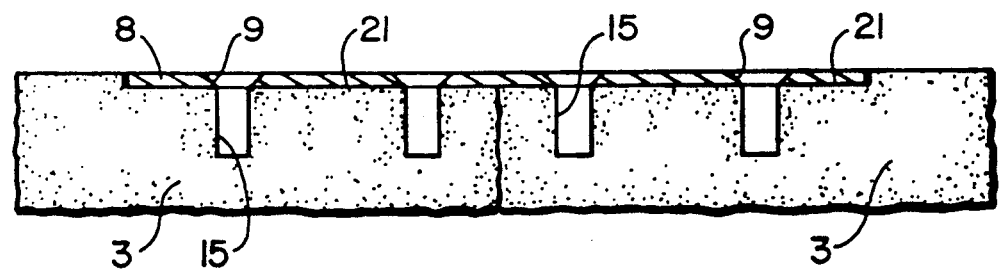
FIG. 8 is a view similar to FIG. 7 showing an attaching plate positioned in the recess.
Figure 10:
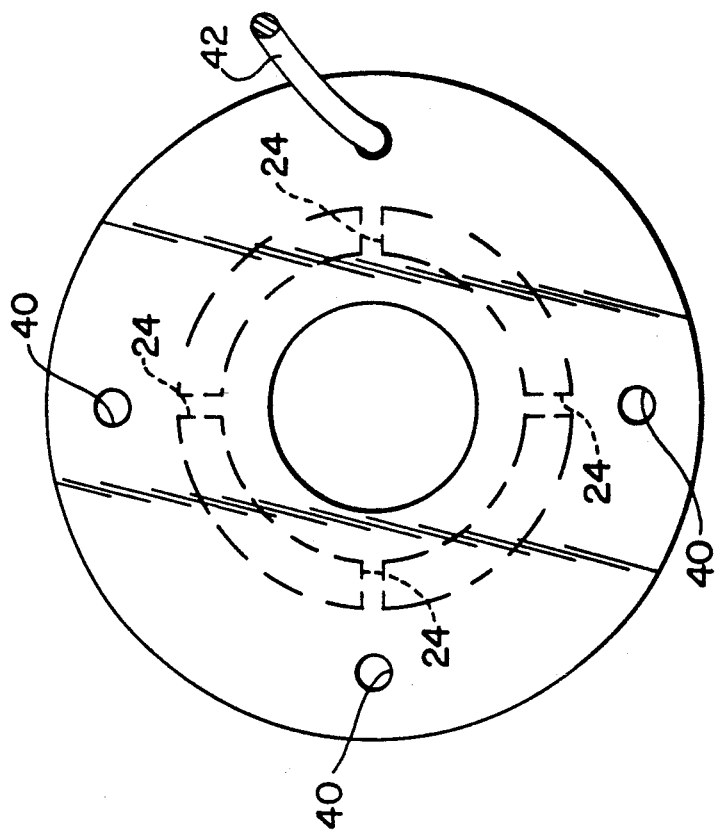
FIG. 10 is a top view of FIG. 9.

With some fractures, or a pair of bone fragments, a plate 8 is placed across the fracture, or between the bone fragments; holes 9 are placed in the plate on each side of the fracture and a hole 15 is drilled in the bone 3 aligned with each hole 9. Holes 9 can have tapered sides to receive a rivet having a tapered surface 6B for a flush installation. A rivet assembly, rivet 2 and puller member 4, are inserted through each hole 9 into its aligned hole 15 and pulled to connect the plate 8 to the bone 3. In some instances, a recess 21 is made in bone being attached to receive the plate 8 (see FIGS. 7 and 8).

It is desirable that the upper annular portion 10 of the rivet 2 be of such a length that the top of the "holding" expansion of the rivet 2 is formed below the surface of the bone to obtain the proper holding location. This length places the annular stop 14 below the surface layer of the bone to form the top of the "holding" expansion. It can be seen that the puller head 20, when in position against annular stop 14, will hold the top of the ribs 13A outwardly in their expanded position, as shown in FIG. 5, or in their radially extended position, as shown in FIG. 6. This is also true of intermediate positions. This positioning of puller head 20 aids in preventing withdrawal of the rivet 2.

Figure 9:
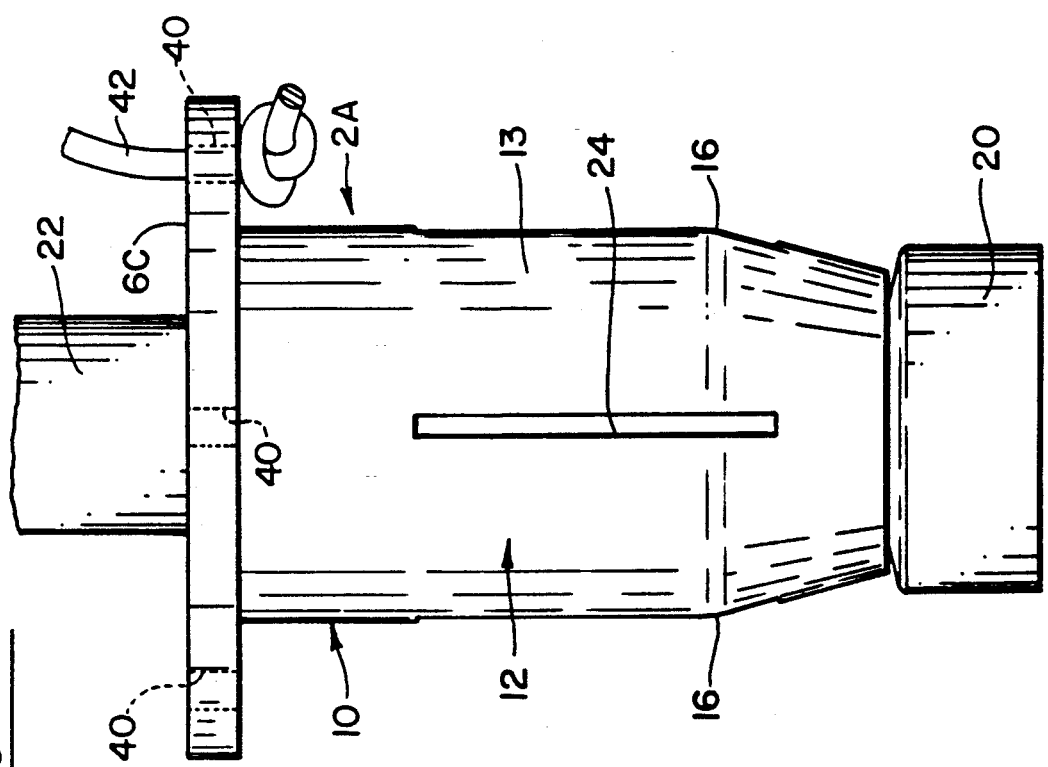
FIG. 9 is a view similar to FIG. 1 showing a bone rivet with a larger top flange with means to attach a suture.

FIG. 9 shows a bone rivet device with a rivet 2A having an enlarged top 6C. Means are provided on top 6C to attach a suture.

Four holes 40 are placed around the top 6C to affix a suture 42. A single suture 42 can be affixed to one hole 40 by being tied as in FIG. 9. A suture 42 can be threaded through two holes 40 from one side making two suture ends available. A barb, or projection, 27, can be provided on one or more ribs 13A to aid in maintaining the rivet 2 in place (see FIG. 14).

Figure 11:
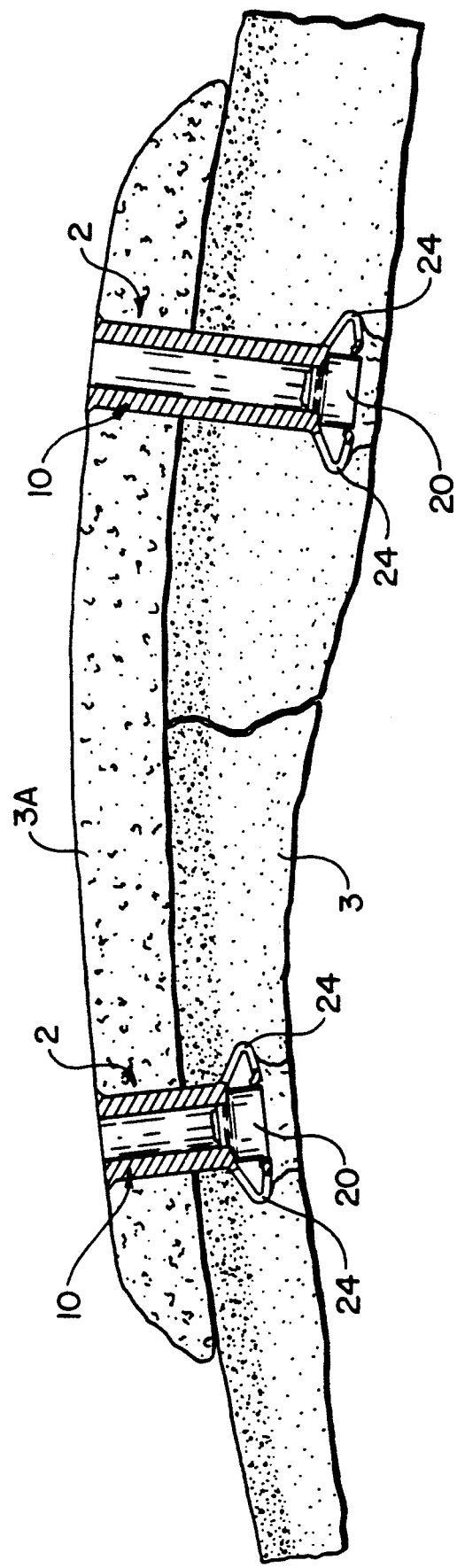
FIG. 11 is a cross-sectional view of a bone graft bridging a fracture, said bone graft being maintained in place by bone rivets of different lengths.

FIG. 11 shows a bone 3A held in position to form a bone graft on a bone 3. Bone rivets 2 of different lengths are used to place the step, or stop, 14 at a proper location at which to expand the rivet 2. The proper location is determined by the surgeon performing the operation.

FIG. 13 is a modification of a rivet 2 in which undercut sections 17 on ribs 13A provide a weakened location which would permit the ribs 13A to bend outwardly if the wall of the hole in which the rivet is located was "soft" enough.

Bone rivet assemblies having the same length are shown in FIGS. 16, 16A and 16B and have different lengths of upper annular portion 10 and different lengths of lower annular portion 12 for use in controlling the area of expansion.

As shown in FIG. 6, the projection of ribs 13A into the "soft" bone 3 forms arms of various shapes with the bend starting at circumferential line 16 depending on the density of the bone. As the arms form, the puller head 20 bends the end of the solid tapered portion 26 inwardly and pulls within the end of the rivet 2 for the top surface 19 to engage the stop 14 and limit the expansion of the rivet.

While the principles of the invention have now been made clear in an illustrative embodiment, it will become obvious to those skilled in the art that many modifications in arrangement are possible without departing from those principles. The appended claims are, therefore, intended to cover and embrace any such modifications, within the limits of the true spirit and scope of the invention.

We claim:

1. An expandable rivet for expanding in a hole, said rivet having a cylindrical body with an exterior surface for fitting in a hole, said cylindrical body having a top and a bottom, a radial projection means at the top of said cylindrical body for contacting the edge of a hole to control the extent the cylindrical body extends into a holes said cylindrical body having a longitudinal opening extending therethrough, a top portion of said cylindrical body having the opening with a first diameter for receiving a puller rod, a bottom portion of said cylindrical body below said top portion having the opening with a second diameter greater than the first diameter, said cylindrical body having an annular step facing downwardly where the two diameters of the opening meet forming a stop for a puller head, said bottom portion of said cylindrical body having a plurality of longitudinal slots therein extending between the exterior surface and the opening extending therethrough forming ribs, the lower part of said bottom portion being tapered inwardly to its end, a solid annular ring at the bottom of said tapered bottom portion connecting to the ribs, said solid annular ring having a bottom annular surface, said annular surface being tapered outwardly and downwardly for being contacted by a puller head for rivet expansion.

2. An expandable rivet assembly for expanding in a hole, a rivet having a cylindrical body with an exterior surface for fitting in a hole, said cylindrical body having a top and a bottom, a radial projection means at the top of said cylindrical body for contacting the edge of a hole to control the extent the cylindrical body extends into the hole, said cylindrical body having a longitudinal opening extending therethrough, a puller for expanding said rivet extending through said opening, said puller having a puller rod with a puller head, said puller rod extending above the top of said cylindrical body, said puller head being below the bottom of said cylindrical body, a top portion of said cylindrical body having the longitudinal opening with a first diameter receiving said puller rod with a slidable fit, a bottom portion of said cylindrical body below said top portion having the longitudinal opening with a second diameter greater than the first diameter, said cylindrical body having an annular step facing downwardly where the two diameters of the opening meet forming a stop for the puller head, said bottom portion of said cylindrical body having a plurality of longitudinal slots therein extending between the exterior surface and the opening extending therethrough forming ribs, said bottom portion of said cylindrical body having a bottom annular surface, said puller head having a third diameter greater than the second diameter of the opening, said puller head having a top surface for engaging and acting against said bottom annular surface of said cylindrical body to expand the exterior surface of the bottom portion of said cylindrical body outwardly when the puller rod is pulled upwardly, said stop for the puller head limiting the upward expansion of the rivet, the lower part of said bottom portion of said cylindrical body being tapered inwardly to its end.

3. An expandable rivet assembly as set forth in claim 2 including a solid annular ring at the bottom of said tapered bottom portion.

4. An expandable rivet assembly as set forth in claim 2 for expanding in a hole in material of varying density, said cylindrical body of said rivet having two ways to expand, one is to expand as radially extending arms into the material and the other is to expand radially as a larger cylinder compressing the material; when said puller head acts against said bottom annular surface of said cylindrical body to expand it, if the bottom portion of said cylindrical body is against material of low density said ribs will extend as arms into the material by the puller head; if the bottom portion of said cylindrical body is against material of high density said bottom portion of said cylindrical body will expand radially as a larger cylinder compressing the high density material by the puller head being pulled within said bottom portion of said cylindrical body to expand said bottom portion of said cylindrical body; said puller stopping expansion when it contacts said stop.

5. An expandable rivet assembly as set forth in claim 4 wherein the material is bone.

6. An expandable rivet for expanding in a hole, said rivet having a cylindrical body with an exterior surface for fitting in a hole, said cylindrical body having a top and a bottom, a radial projection means at the top of said cylindrical body for contacting the edge of a hole to control the extent the cylindrical body extends into a hole, said cylindrical body having a single longitudinal opening extending therethrough, a top portion of said cylindrical body having the single longitudinal opening with a first diameter for receiving a puller rod, a bottom portion of said cylindrical body below said top portion having the single longitudinal opening with a second diameter greater than the first diameter, said cylindrical body having an inner annular step facing downwardly where the two diameters of the single longitudinal opening meet forming a stop for a puller head, said bottom portion of said cylindrical body having a plurality of longitudinal slots therein extending between the exterior surface and the opening extending therethrough forming ribs, the lower part of said bottom portion of said cylindrical body being tapered inwardly to its end for contacting a puller head, a solid annular ring at the bottom of said tapered bottom portion connecting the ribs, said solid annular ring having a bottom annular surface, said annular surface being tapered for being contacted by a puller head for directing the tapered end of said annular ring radially.

7. An expandable rivet assembly as set forth in claim 6 wherein said hole is in bone.

8. An expandable rivet assembly as set forth in claim 6 wherein said annular surface is tapered outwardly and downwardly.

9. An expandable rivet for expanding in a hole, a rivet having a cylindrical body with an exterior surface for fitting in a hole, said cylindrical body having a top and a bottom, a radial projection means at the top of said cylindrical body to control the extent the cylindrical body extends into a hole, said cylindrical body having a longitudinal opening extending therethrough, a puller extending through said opening for expanding said rivet, said puller having a puller rod with a puller head, said puller rod extending above the top of said cylindrical body, said puller head being positioned below the bottom of said cylindrical body, a top portion of said cylindrical body having the longitudinal opening with a first diameter receiving said puller rod with a slidable fit, a bottom portion of said cylindrical body below said top portion having the longitudinal opening with a second diameter greater than the first diameter, said puller head having a top annular surface, said cylindrical body having an annular step facing downwardly in said longitudinal opening where the two diameters of the opening meet an upward annular stop for the top annular surface of the puller head, said cylindrical body below said top portion having a plurality of longitudinal slots therein extending between the exterior surface and the opening extending therethrough forming ribs, the lower part of said bottom portion of said cylindrical body being tapered inwardly to its end, said bottom portion of said cylindrical body having a bottom annular surface, said top annular surface of said puller head being aligned with said bottom annular surface of said cylindrical body for engaging and acting against said bottom annular surface to radially expand the ribs of the exterior surface of said cylindrical body outwardly when the puller rod is pulled upwardly, said annular stop for the puller head being aligned with said top annular surface of said puller head limiting the radial expansion of the rivet by limiting the upward pull of the puller head to below said annular stop.

* * * * *